United States Patent [19]

Sarantakis

[11] 4,098,782
[45] Jul. 4, 1978

[54] (HIS⁵)-SOMATOSTATIN AND ANALOGUES THEREOF

[75] Inventor: Dimitrios Sarantakis, West Chester, Pa.

[73] Assignee: American Home Products Corporation, New York, N.Y.

[21] Appl. No.: 777,261

[22] Filed: Mar. 14, 1977

[51] Int. Cl.² .................... C07C 103/52; A61K 37/02
[52] U.S. Cl. ............................. 260/112.5 S; 424/177
[58] Field of Search ................. 260/112.5 S; 424/177

[56] References Cited
PUBLICATIONS

C. Meyer, et al., Biochem. and Biophys. Res. Commun. 74, No. 2, 1977, pp. 630–636.

Primary Examiner—Delbert R. Phillips
Attorney, Agent, or Firm—Richard K. Jackson

[57] ABSTRACT

Polypeptides of the formula:

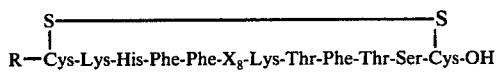

R—Cys-Lys-His-Phe-Phe-X₈-Lys-Thr-Phe-Thr-Ser-Cys-OH the linear precursor intermediates and non-toxic acid addition salts thereof, wherein:

R is hydrogen, lower alkanoyl, benzoyl, Ala-Gly-, Gly-Gly-Gly-, Ala-D-Ala- or p-Glu; and X₈ is L-Trp or D-Trp are described. (His⁵)-Somatostatin and its analogues inhibit the release of growth hormone and glucagon without materially affecting the secretion of insulin, and are useful in the treatment of diabetes, acromegaly and hyperglycemia.

4 Claims, No Drawings

(HIS⁵)-SOMATOSTATIN AND ANALOGUES THEREOF

DESCRIPTION OF THE INVENTION

In accordance with this invention there is provided a group of polypeptides of the following formula:

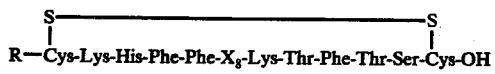

the linear precursor intermediates and non-toxic acid addition salts thereof, in which:

R is hydrogen, lower alkanoyl, benzoyl, Ala-Gly-, Ala-D-Ala-, or p-Glu; and $X_8$ is L-Trp or D-Trp These compounds inhibit the secretion of growth hormone and glucagon without materially affecting the secretion of insulin, and like somatostatin, they are useful in the treatment of diabetes mellitus, acromegaly and hyperglycemia.

The polypeptides of this invention are produced by the well known solid phase method as described by Stewart et al., Solid Phase Peptide Synthesis, Freeman and Co., San Francisco, 1969. As applied to the compounds of this invention, α-amino and sulfhydryl protected cysteine is attached to a chloromethylated polystyrene resin followed by removal of the α-amino protecting group with trifluoroacetic acid in methylene chloride, trifluoroacetic acid alone or HCl in dioxane. The deprotection is conducted at a temperature between about 0° C. and room temperature. Other standard cleaving reagents and conditions for removal of specific α-amino protecting groups may be used as described in Schroder E. Lubke, "The Peptides", 1, 72–75 (Academic Press, 1965). After removal of the α-amino protecting group the subsequent protected amino acids are coupled individually to the resin supported sequence, seriatim. Alternatively, small peptide fragments may be prepared by the solution method and introduced into the solid phase reactor in the desired order. Each protected amino acid or amino acid sequence is introduced into the solid phase reactor in about a four fold excess. The coupling is carried out in dimethylformamide, methylene chloride, or a mixture of the two solvents. The success of each coupling reaction at each stage of the synthesis is determined by the ninhydrin reaction as described by E. Kaiser et al., Analyt. Biochem., 34, 595 (1970). Where incomplete coupling has occurred, the reaction is repeated before the α-amino protecting group is removed for introduction of the next amino acid or amino acid sequence. The coupling reagents employed were N-hydroxybenzotriazole and diisopropylcarbodiimide.

After the desired amino acid sequence has been synthesized, the polypeptide is removed from the resin support by treatment with hydrogen fluoride and anisole to obtain the fully deprotected linear polypeptide. The cyclic disulfide is produced by air oxidation.

Non-toxic acid addition salts of the linear and cyclic polypeptides are produced by methods well known in the art from hydrochloric, hydrobromic, sulfuric, phosphoric, polyphosphoric, maleic, acetic, citric, benzoic, succinic, malonic, or ascorbic acid and the like.

The protecting groups employed throughout the solid phase synthesis are well known to the art. In selecting a particular side chain protecting group to be used in the synthesis of the peptides of this invention, the following rules should be followed: (a) the side chain protecting group must be stable to the reagent and under the reaction conditions selected for removing the α-amino protecting group at each step of the synthesis, (b) the protecting group must retain its protecting properties (i.e. not be split off under coupling conditions), and (c) the side chain protecting group must be removable upon the completion of the synthesis containing the desired amino acid sequence under reaction conditions that will not alter the peptide chain.

The following Example illustrates the preparative technique applicable in the production of the compounds of this invention. By introducing tert-butyloxycarbonyl protected D-tryptophan into the solid phase reactor as th seventh amino acid introduced, the compounds corresponding to D-trp as $X_8$ in the generic formula, supra, are produced. Similarly by omitting the N-terminal Boc-Ala-Gly-OH group or by introducing a lower alkanoic acid, benzoic acid, Boc-Gly-Gly-Gly-OH, Boc-Ala-D-Ala-OH, or p-Glu-OH into the solid phase reactor as the thirteenth amino acid moiety in lieu of the illustrated Boc-Ala-Gly-OH group, there is obtained the corresponding polypeptide variables on the $Cys^3$ group. The fully protected intermediate containing the D-Trp⁸ unit, corresponding to the illustrative compound prepared in the following example is:

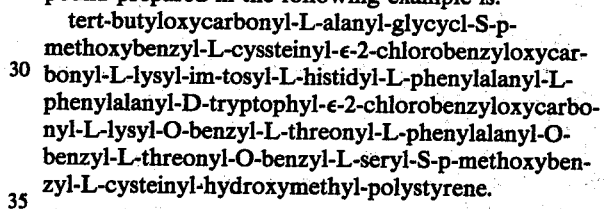

EXAMPLE

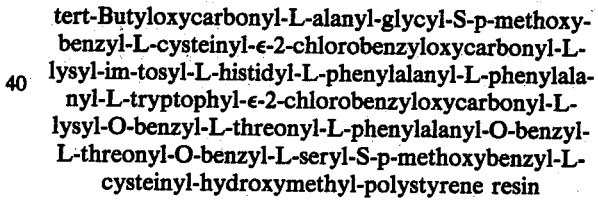

Chloromethylated polystyrene resin (Lab Systems, Inc.) 1% cross-linked with divinylbenzene was esterified with Boc-Cys-(SMBzl)OH according to Gisin, Helv. Chim. Acta, 56, 1976 (1973). The polystyrene resin ester was treated according to schedule A for the incorporation of Boc-Ser(Bzl)-OH, Boc-Thr(Bzl)-OH, Boc-Phe-OH, Boc-Thr(Bzl)-OH, Boc-Lys(ClCBZ), Boc-Trp-OH, Boc-Phe-OH, Boc-Phe-OH, Boc-His(-Tos)-OH, Boc-Lys(ClCBZ)-OH, Boc-Cys(SMBzl)-OH, Boc-Ala-Gly-OH to afford the title peptidoresin.

Schedule A
1. wash with $CH_2Cl_2 \times 3$
2. treat with TFA-$CH_2Cl_2$-DTE (1:2:0.5%) for 5 min.
3. treat with TFA-$CH_2Cl_2$-DTE (1:2:0.5%) for 25 min.
4. wash with $CH_2Cl_2 \times 3$
5. wash with DMF
6. treat with 12% TEA in DMF twice for 3 min.
7. wash with DMF
8. wash with $CH_2Cl_2 \times 3$
9. treat with 4 equivalents of the corresponding amino acid derivative in $CH_2Cl_2$-DMF and 4 equivalents of N-hydroxybenzotriazole and stir for 5 min.
10. add in two portions 5 equivalents of DIC dissolved in CH$_2$Cl$_2$ over a period of 30 minutes; reaction time 12–18 hours
11. wash with DMF ×3
12. wash with CH$_2$Cl$_2$ × 3
13. test ninhydrin reaction according to Kaiser et al., Annal. Biochem., 34, 595 (1970). In case of incomplete reaction repeat lines 9 to 13 as above.

L-Alanyl-glycyl-L-cysteinyl-lysyl-L-histidyl-L-phenylalanyl-L-phenylalanyl-L-tryptophyl-L-lysyl-L-threonyl-L-phenylalanyl-L-threonyl-L-seryl-L-cysteine(3–14 cyclic)disulfide The peptidoresin of the previous paragraph (11.6 g.) was mixed with 10 ml. anisole and treated with liquid hydrogen fluoride for 40 minutes in an ice-bath. The excess hydrogen fluoride was removed as fast as possible under vacuo and the residue was taken in 50% aq. AcOH, and filtered, The filtrate was washed with ether and the aqueous layer was diluted with a large volume of dearated water (ca. 3 lts.) The pH was adjusted to 7.4 and left to stand in the air for 48 hours then it was acidified with gl. AcOH to pH 6.5 and lyophilized to yield 4.7 g. of solid.

Part of this crude material was chromatographed through Sephadex G-10 column (2.5 × 55 cm) and eluted with 2 M aq. AcOH. The fractions (3.5 ml.) which emerged in tubes 150 to 230 (330 mg.) was applied onto a column of Sephadex G-25 which was equilibrated with the lower phase of a mixture of n-butanol-water-gl. AcOH, 4:5:1, and then with the upper phase. The column was eluted with the upper phase and the material which emerge in tubes 120–170 was pooled and lyophilized to afford the title compound, 18.3 mg.

R$_f$(n-butanol-water-gl. AcOH, 4:5:1) 0.32

R$_f$ (n-butanol-water-gl. AcOH-pyridine, 30:24:6:20) 0.67

Amino acid analysis Thr (2) 2.06, Ser (1) 1.21, Gly (1) 0.43, Ala (1) 1.03, Cys (2) 1.48, Phe (3) 3, His (1) 0.94, Lys (2) 1.84, Trp N.D.

The activity of the product of the preceding preparatory example, (His$^5$) Somatostatin, was determined by the following procedure:

Albino male rats were administered Nembutal intraperitoneally at a dose of 50 milligrams per kilogram. Fifteen minutes later a subcutaneous injection of the test compound or physiological saline was administered. Ten minutes later 0.5 milliliters of arginine (300 milligrams per milliliter, pH 7.2) is injected into the heart. Five minutes after receipt of the arginine the rats are decapitated and blood is collected into trasylol-EDTA. An appropriate aliquot was assayed for growth hormone, insulin and glucagon. The results of the assay are as follows:

| Compound | Dose ug/kg | GH ug/ml | Insulin μU/ml | Glucagon pg/ml |
|---|---|---|---|---|
| (His$^5$)SRIF | 1300 | 83 ± 15* | 390 ± 94 | 31 ± 6* |
| SRIF | 200 | 66 ± 11* | 232 ± 23+ | 26 ± 6* |
| Control | — | 288 ± 30 | 372 ± 47 | 51 ± 4 |

\* = p < 0.01
+ = p < 0.05

Thus, (His$^5$) Somatostatin, representative of the other compounds of the invention is an effective agent for reducing secretion of growth hormone and glucagon without materially affecting insulin levels.

The compounds described herein may be administered to warm blooded mammals, including humans, either intravenously, subcutaneously, intramuscularly, or orally to inhibit the release growth hormone and glucagon where the host being treated requires therapeutic treatment for excess secretion of those substances as is frequently associated with conditions such as juvenile diabetes, hyperglycemia and acromegaly. the required dosage will vary with the particular condition being treated, the severity of the condition and the duration of treatment. If the active ingredient is administered in tablet form the tablet may contain: a binder such as gum tragacanth, corn starch, gelatin; and excipient such as dicalcium phosphate; a disintegrating agent such as corn starch, alginic, acid, etc.; a lubricant such as magnesium stearate; and a sweetening and/or flavoring liquid carriers for intravenous administration include isotonic saline, phosphate buffer solutions, etc.

What is claimed is:

1. A polypeptide of the formula:

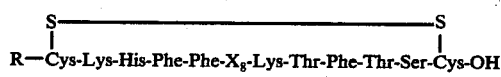

the linear precursor intermediates and non-toxic acid addition salts thereof, in which:
R is hydrogen, lower alkanoyl, benzoyl, Ala-Gly-, Ala-D-Ala-, or p-Glu; and
X$_8$ is L-Trp or D-Trp.

2. A polypeptide of claim 1 of the formula:

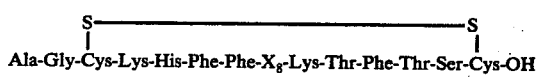

its linear precursor intermediates or a non-toxic acid addition salt thereof in which X$_8$ is L-Trp or D-Trp.

3. The polypeptide of claim 2 which is L-alanyl-glycyl-L-cysteinyl-L-lysyl-L-histidyl-L-phenylalanyl-L-phenylalanyl-L-tryptophyl-L-lysyl-L-threonyl-L-phenylalanyl-L-threonyl-L-seryl-L-cysteine or a non-toxic acid addition salt thereof.

4. The polypeptide of claim 2 which is L-alanyl-glycyl-L-cysteinyl-L-lysyl-L-histidyl-L-phenylalanyl-L-phenylalnyl-L-tryptophyl-L-lysyl-L-threonyl-L-phenylalanyl-L-threonyl-L-seryl-L-cysteine (cyclic 3–14 disulfide) or a non-toxic acid addition salt thereof.

* * * * *